United States Patent [19]

Braithwaite

[11] Patent Number: 5,066,280

[45] Date of Patent: Nov. 19, 1991

[54] SYRINGES

[75] Inventor: Philip W. Braithwaite, Strensham, England

[73] Assignee: Technosystem Limited, Liverpool, United Kingdom

[21] Appl. No.: 469,418

[22] PCT Filed: Sep. 30, 1988

[86] PCT No.: PCT/GB88/00803

§ 371 Date: May 17, 1990

§ 102(e) Date: May 17, 1990

[87] PCT Pub. No.: WO89/02759

PCT Pub. Date: Apr. 6, 1989

[30] Foreign Application Priority Data

Sep. 30, 1987 [GB] United Kingdom ............... 8722915

[51] Int. Cl.[5] ........................................... A61M 5/00
[52] U.S. Cl. ..................................... 604/110; 604/218
[58] Field of Search ............... 604/110, 218, 187, 228

[56] References Cited

U.S. PATENT DOCUMENTS 4,699,614 10/1987 Glazier ............................... 604/110
4,908,020 3/1990 Pettersen ......................... 604/228 X Primary Examiner—John D. Yasko
Attorney, Agent, or Firm—Young & Thompson

[57] ABSTRACT

A syringe has a barrel 1 housing a plunger 8 linked to a piston incorporating a seal 7 by a coupling member 9. A flange 12 on the coupling member 9 limits the extent of movement of the plunger and piston assembly, in association with latches 16. As the plunger 8 is operated through a sequence of expelling air from the syringe, to draw in liquid into the syringe and then to eject the liquid out again through a needle connected to an outlet 5, camways 11 at the ends of the coupling member 9 operate with projecting keys in such a way that the coupling member 9 is caused to rotate in stages. Then after the plunger is withdrawn again (after ejection of the liquid) the projecting keys 10 on the part associated with the piston seal 7 will become detached from the relevant keyways 11 so that the syringe cannot be used a second time.

4 Claims, 6 Drawing Sheets

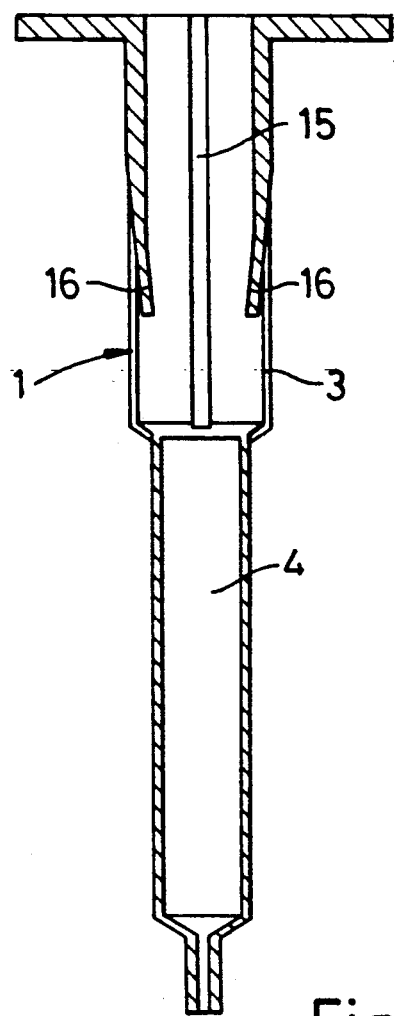
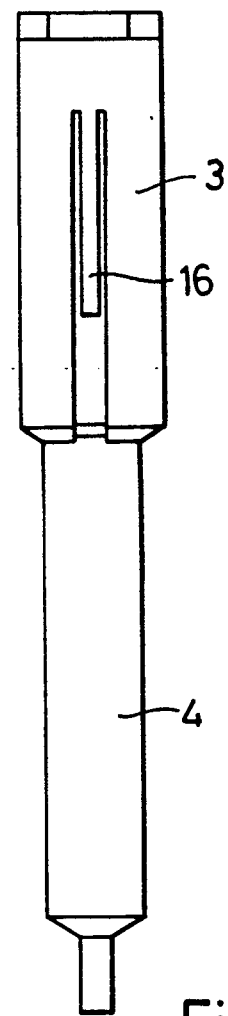
Fig. 2A  Fig. 2B
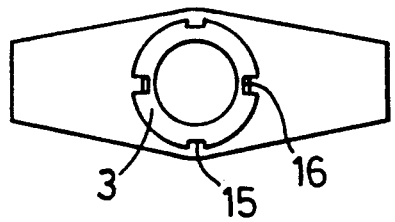
Fig. 2C

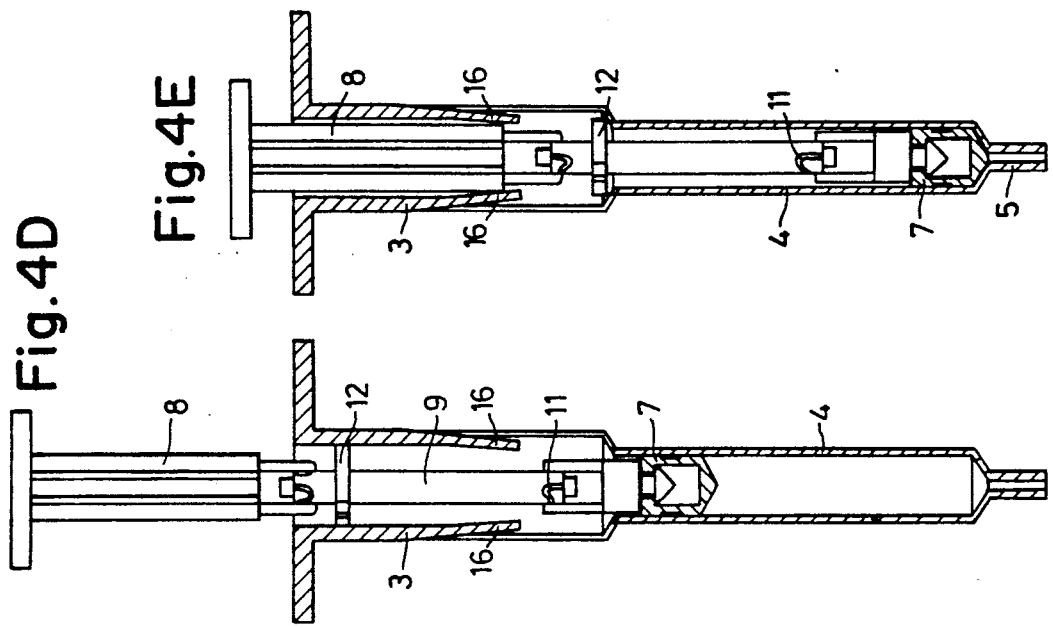

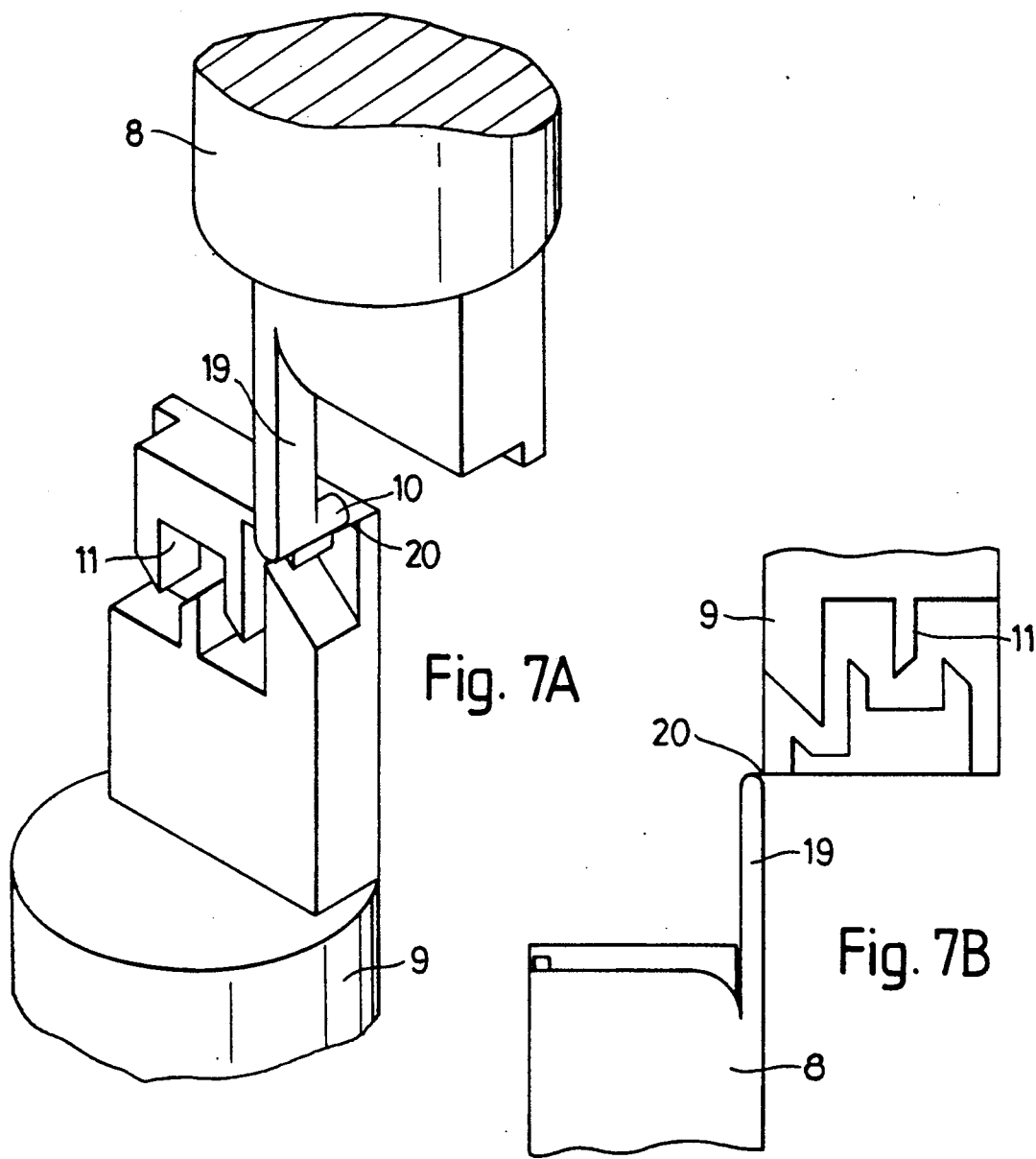

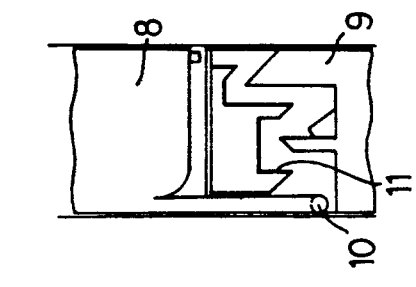
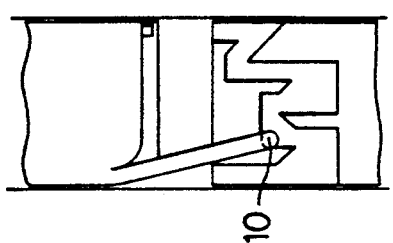
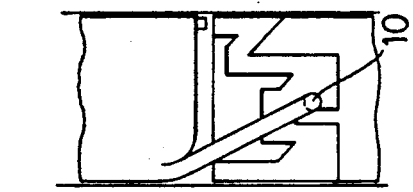
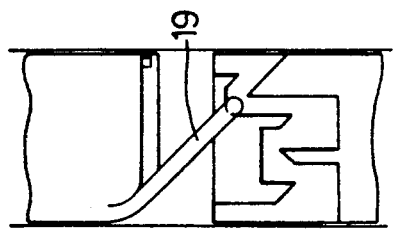
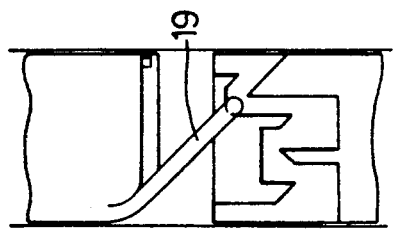
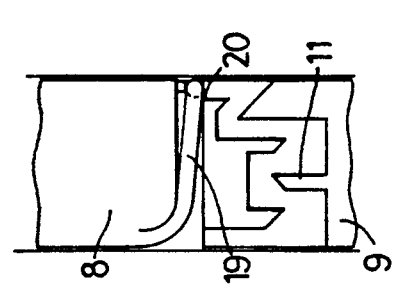
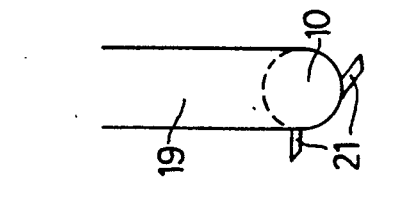
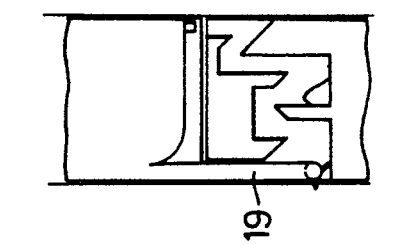
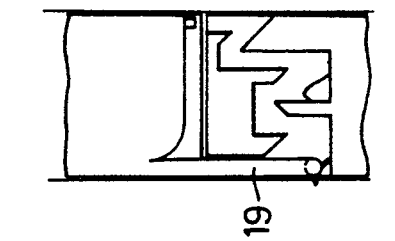
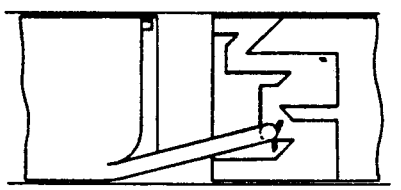
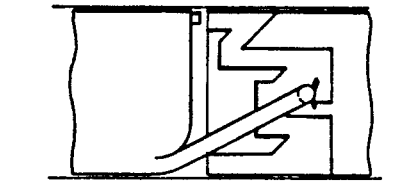
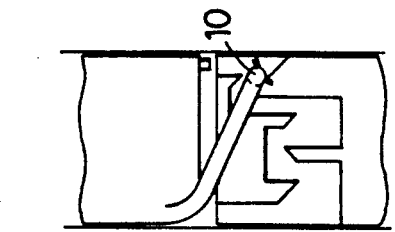
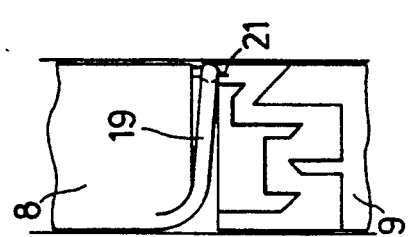

SYRINGES

This invention relates to syringes and in particular to so-called disposable syringes, which are used in general medical practice as an effective way of preventing cross-infection. However, due to shortages of these products, and possibly ignorance, there is a tendency, particularly in the Third World, to use the syringe maybe five or six times before throwing it away. Drug users also commonly share syringes, which are used many times, because they do not have access to a regular supply.

It is an object of this invention to provide a disposable syringe which is effective in operation, can be used in a conventional manner, is cheap to produce and will deter attempts to reuse the syringe.

According to the invention there is provided a syringe comprising a barrel housing both a piston and a plunger for moving the piston to enable a liquid to be drawn in to and ejected from a portion of the barrel, the piston and plunger being interconnected by a decoupling linkage such that the plunger is operatively disconnected from the piston after the plunger has been retracted and subsequently depressed.

In the preferred arrangement the piston and the plunger are interconnected by a coupling member. In this case the coupling member may be interconnected to both the piston and the plunger by a decoupling linkage. Ideally the piston or the coupling member carries a flange which interacts with latches on the inner wall of the barrel so as to be able to pass the latches before disconnection of the or each decoupling linkage but is unable to pass the latches upon attempted withdrawal of the plunger after such disconnection. The latches may, for example, be in the form of inwardly projecting serrated ribs on inwardly sprung-loaded arms. Preferably, the flange will incorporate keyways which can ride up the latches whilst the flange is in one rotational attitude, the latches abutting the flange when the flange is in alternative rotational attitudes. In this case the or each decoupling linkage will ideally be effective to cause rotation of the part carrying the flange upon application of reciprocation movements to the plunger. It will be understood that any connection means which fulfils this function is applicable. For example, the or each decoupling linkage may be threadedly engaged and the piston may be interconnected with the barrel of the syringe so that it is caused to rotate during axial movement, the threaded engagement being such that on a second retraction of the plunger the piston and plunger become disengaged.

In the preferred embodiment the or each decoupling linkage includes a camway on one part for receiving a cam follower on the other part, the camway being shaped such that movement of the plunger causes relative movement between the cam follower and the camway, whereby the cam follower is removed from the camway on a second retraction of the plunger.

The cam followers may, for example, be diametrically opposed pins, locating in a ring having the camway formed on an inner surface. These pins may, with advantage be positioned at the ends of fingers which are flexible but biased in the axial position of the piston, so that the pins will be biased to follow the camways in one direction only. Additionally the pins may carry projecting webs which resist movement of the pins in the other direction through the camway.

If desired the parts of the or each decoupling linkage defining the camway and the cam follower respectively may be biased apart by a spring or other biasing means.

The plunger and piston may be keyed together for rotational movement but separable on retraction after disconnection of the decoupling linkage. The syringe may include one or more cover plates for preventing access to the decoupling linkage after operative disconnection of the piston and plunger. Where the plunger can be full withdrawn from the syringe it may be hollow so that it can be used as a needle cover to prevent infection spreading, due to accidental scratches during subsequent handling.

The mechanism employed in the syringes of this invention is such that the syringe can be handled and operated in the conventional manner, without any additional special movements, in order to deliver an injection satisfactorily and in accordance with correct practice.

The invention may be performed in various ways and preferred embodiments thereof will now be described with reference to the accompanying drawings, in which:

FIGS. 2A, 2B and 2C are respectively a vertical section, a side view and a a top view of a syringe barrel of the syringe shown in FIG. 1;

FIGS. 4A to 4E illustrate various stages of operation of the syringe shown in FIG. 1;

FIGS. 7A and 7B show, in perspective and side view respectively; an alternative type of coupling arrangement for the plunger and piston unit of the syringe shown in FIG. 1;

FIGS. 8A to 8F illustrate stages of operation of the coupling arrangement shown in FIG. 7;

FIGS. 9A to 9F show comparable stages of operation of a modified form of coupling arrangement, whilst FIG. 9G shows the modification on a larger scale; and FIG. 10 illustrates a further modification to the coupling arrangement shown in FIG. 7.

Figure 1:
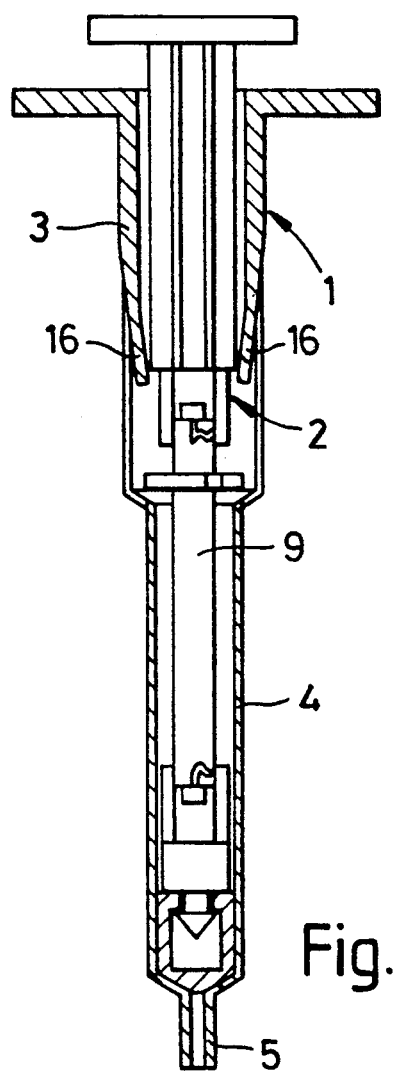
FIG. 1 is a vertical section through one embodiment of an assembled syringe of this invention.
Figure 3A:
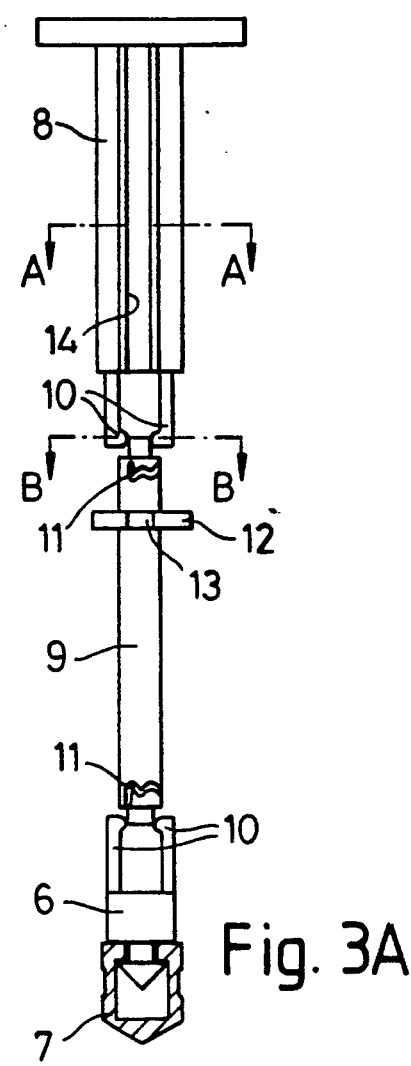
FIGS. 3A, 3B and 3C are respectively side views and sections on lines A—A and B—B of the plunger and piston unit of the syringe of FIG. 1.
Figure 3B:
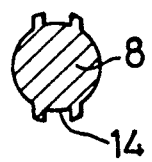
Figure 3C:
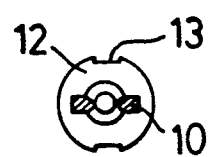

Referring now to FIGS. 1 to 3, the preferred form of syringe comprises a syringe barrel 1 enclosing a plunger and piston unit 2. The barrel 1 has an upper plunger housing 3 and a lower piston housing 4 leading to an outlet 5 which will receive the syringe needle. The unit 2 has, at its lower end, a seal mount 6 carrying a piston seal 7. The mount 6 is linked to a plunger 8 by a coupling 9. The interconnection of the coupling 9 to the mount 6 and the plunger 8 is achieved by means of a pair of projecting keys 10 on those two parts received within camways 11 at the two ends of the coupling 9.

The coupling 9 also incorporates a flange 12 provided with a pair of keyways 13. The plunger 8 incorporates a pair of tracks 14 formed down the sides which engage with ribs 15 projecting in from the side walls of the plunger housing 3 which ensures that the plunger does not rotate as it is raised and lowered within the plunger housing 3. The plunger housing 3 also incorporates inwardly biased sprung latches 16 which will fit within the keyways 13 of the flange 12 on the coupling 9. The latches 16 can be forced apart by the portion of the flange 12 of greater diameter but will snap inwardly above the larger diameter portion of the flange 12 once the flange has been moved below the latches.

Use of the syringe is illustrated in FIG. 4. The completely assembled plunger and piston unit 2 will be introduced into the barrel 1, with the tracks 14 sliding down the ribs 15, as shown in FIG. 4A. The keys 10 are manufactured with thin connecting pieces which attach the keys to the ends of the coupling 9 and when the plunger 8 is pushed fully home, these connecting pieces will shear so that the keys 10 enter the camways 11, as shown in FIG. 4B.

Retraction of the plunger 8 (FIG. 4C) causes the keys 10 to enter into subsequent sections of the camways 11 which forces the coupling 9 to rotate into a condition wherein the keyways 13 on the flange 12 are aligned with the latches 16. Further withdrawal of the plunger 8 causes the flange 12 to ride up the latches 16 until the flange 12 enters the upper portion of the plunger housing 3 of largest internal diameter where the flange 12 is freely rotatable (FIG. 4D).

Finally, depression of the plunger 8, causes the keys to move into further sections of the camways 11 resulting in further rotation of the coupling 9 (FIG. 4E). This also results in ejection of a dose drawn into the piston housing 4 during the previous stage, and in the flange 12 being forced past the spring-like latches 16. Any attempt to withdraw the plunger 8 (by more than a fairly small amount) will be defeated since the flange 12 will now abut against the latches 16 and cannot pass these latches because the keyways 13 in the flange have been rotated out of alignment with the latches 16.

It will be appreciated that during the steps illustrated in FIGS. 4A to 4E, air will be expelled from the syringe, the required dose will be drawn into the piston housing 4 and will then be ejected through the needle attached to the outlet 5 upon final depression of the plunger 8. Further use of the syringe is prevented because the coupling 9 cannot again be withdrawn within the plunger housing 3, and in any case is decoupled from the piston seal 7.

Figure 5:
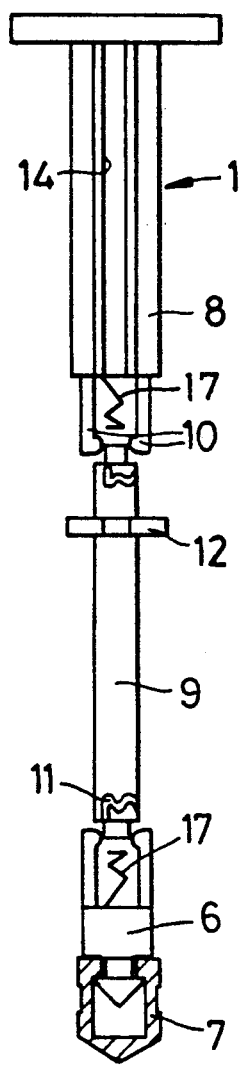
FIG. 5 shows a modification to the design of the plunger and piston unit of the syringe shown in FIG. 1.

FIG. 5 illustrates the incorporation of spring members 17 (which can be formed as part of the original moulding) which bias the seal mount 6 and the plunger 8 away from the coupling 9. These springs 17 ensure that the keys 10 follow the paths through the camways 11 if the piston housing 4 is filled with a dose by means of pressure from a pressurised vial, rather than by pulling on the plunger 8. Again, however, in the initial stage, the plunger and piston unit 2 will be introduced into the barrel 1 and pressed fully home so as to shear the connecting pieces between the keys 10 and the ends of the coupling 9.

Figure 6A:
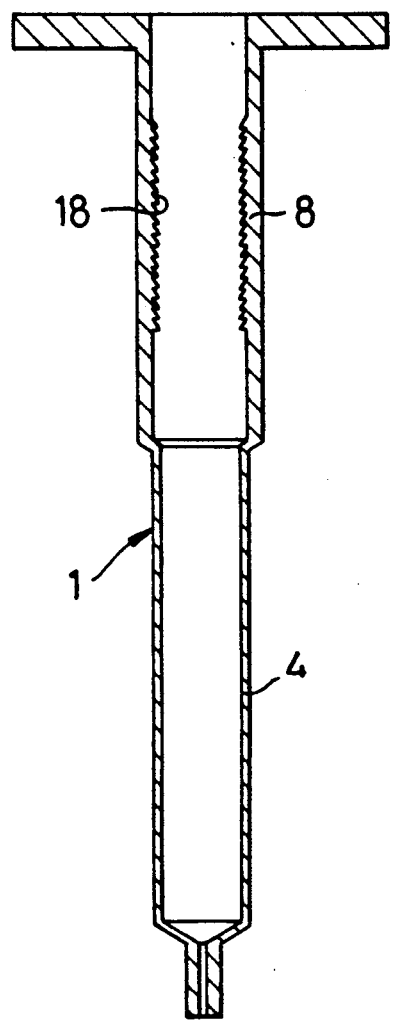
FIGS. 6A and 6B are a vertical section and a top view respectively of a modified barrel for the syringe shown in FIG. 1.
Figure 6B:
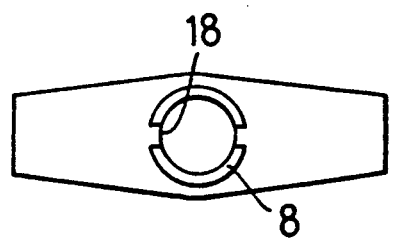

FIGS. 6A and 6B illustrate a modified form of barrel wherein the latches 16 are replaced by serrated keys 18. Once the plunger 8 has been withdrawn into the condition illustrated in FIG. 4D subsequent depression of the plunger 8 will cause the flange 12 to move past the serrations in the keys 18 in the manner of a ratchet type mechanism. This prevents the unethical user from delivering reduced doses of vaccine by attempting to avoid full operation of the latches as in the type of syringe construction illustrated in FIG. 1. As an alternative, modified forms of latches could be provided to overcome this problem.

An alternative type of coupling arrangement is illustrated in FIGS. 7A and 7B. Here each key 10 is carried at the end of a spring section finger 19. There is a single key 10 for each part 6 or 8. Again, during initial manufacture the keys 10 are attached to parts of the coupling 9 by thin connecting pieces, namely at the point 20. The shape of the camway 11 can be seen clearly from FIG. 7.

FIG. 8 shows the stages of movement of the keys 10 through the camway 11 as the plunger 8 is pushed in and out for the necessary filling and injection of the required dose. As the plunger 8 is pushed downwardly the finger 19 is bent into the position shown in FIG. 8A and is thus sprung loaded. Further downward pressure of the plunger causes the thin connecting piece to break so that the key 10 drops down the first vertical portion of the camway 11, as shown in FIG. 8B. Withdrawal of the plunger then results in the sprung loaded finger 19 moving up the angled portion of the camway 11 (FIG. 8C). This is the condition of the syringe as supplied from the manufacturers to the end user.

Depression of the plunger 8 now causes the key 10 to drop into the lower central portion of the camway 11 (FIG. 8D). This causes air to be expelled from the piston housing 4. The plunger is then withdrawn to cause the dose to be drawn back into the piston housing 4 and the key 10 moves upwardly again and across to the position shown in FIG. 8E. Finally, operation of the syringe to expel the dose causes the key 10 to move into the final portion of the camway 11, where it is free to become released from the coupling 9 should the plunger 8 be withdrawn again. Consequently the piston 7 cannot again be withdrawn.

A slight modification of the arrangement shown in FIG. 7 is illustrated in FIG. 9. As can be seen from FIG. 9G at the end of the finger 19, adjacent to where the key 10 projects, there are provided two projecting webs 21. Both prior to and at the end of a complete operating cycle, one or other of these webs 21 projects and engages with latches 16 (FIG. 2) or serrated keys 8 (FIG. 6). Such webs 10 could also engage within radial grooves formed in the barrel of a syringe. This modified arrangement is particularly suitable for use with a syringe which is to be loaded once only by pressure or suction filling.

As shown in FIG. 10, the finger 19 could be biased by a spring 22 to ensure desired movement of the key 10 through the camway 11 if the syringe is filled by means of pressure from a pressurised vial.

The syringe could be modified in such a way that the full dose must be delivered in one continuous stroke. This would overcome the possibility of unethical users trying to cause, for example, a 2 ml syringe to deliver 4 ×0.5 ml doses to four different patients. Thus the inner face of the plunger housing 3 could be formed with castellations (instead of the serrations of FIG. 6). Then, with the incorporation of the modifications shown in FIGS. 9 and 10, if pressure on the plunger is released, the projecting webs 21 would engage with the castellations. Another possibility is to form the webs 21 from a metal or some other hard material which again has a small degree of flexibility and which is positioned and shaped in such a fashion as to dig into the inner side wall of the plunger housing if pressure on the plunger is released.

A further possible modification would be to construct the plunger on a piston and coupling in such a way that after the final injection stroke the plunger can move towards the piston seal 7, if retracted and depressed again so that, with a proper seal, the plunger would pierce and rupture the seal, thus rendering the syringe unusable.

It will be appreciated that any of the plunger and piston unit assemblies 2 illustrated in the drawings may be used with a conventional syringe barrel. Once the syringe has been used the assembly 2 will break down into its component parts, so that the syringe cannot then be reused as it stands.

I claim:

1. A syringe comprising a barrel housing both a piston and a plunger for moving the piston to enable a liquid dose to be drawn into and ejected from a portion of the barrel, a coupling member interconnecting the piston and the plunger, and decoupling linkages interconnecting the coupling member to at least one of the piston and the plunger such that the plunger is operatively disconnected from the piston after the plunger has been retracted and subsequently depressed, a flange on the piston or the coupling member, and latches on the inner wall of the barrel which interact with the flange so that the flange is able to pass the latches before disconnection of the or each of the coupling linkages but is unable to pass the latches upon attempted withdrawal of the plunger after such disconnection.

2. A syringe according to claim 1 wherein the latches are in the form of inwardly projecting serrated ribs or inwardly spring-loaded arms.

3. A syringe according to claim 1 wherein the parts of the or each decoupling linkage defining the camway and the cam follower respectively are biased apart by a spring or other biasing means.

4. A syringe according to claim 1 wherein the plunger and piston are keyed together for rotational movement but are separable on retraction after disconnection of the decoupling linkage.

* * * * *